(12) United States Patent
Chao

(10) Patent No.: US 10,316,311 B2
(45) Date of Patent: Jun. 11, 2019

(54) ANTIBODY-UREASE CONJUGATES

(71) Applicant: HELIX BIOPHARMA CORP., Richmond Hill (CA)

(72) Inventor: Heman Chao, Richmond Hill (CA)

(73) Assignee: Helix Biopharma Corp., Richmond Hill (CA)

(*) Notice: Subject to any disclaimer, the term of this patent is extended or adjusted under 35 U.S.C. 154(b) by 19 days.

(21) Appl. No.: 14/783,153

(22) PCT Filed: Apr. 3, 2014

(86) PCT No.: PCT/CA2014/050334
§ 371 (c)(1),
(2) Date: Oct. 8, 2015

(87) PCT Pub. No.: WO2014/165985
PCT Pub. Date: Oct. 16, 2014

(65) Prior Publication Data
US 2016/0138002 A1    May 19, 2016

Related U.S. Application Data

(60) Provisional application No. 61/809,842, filed on Apr. 8, 2013.

(51) Int. Cl.
*A61K 47/68* (2017.01)
*C12N 9/96* (2006.01)
*C12N 9/80* (2006.01)
*C07K 16/32* (2006.01)

(52) U.S. Cl.
CPC ............... *C12N 9/80* (2013.01); *A61K 47/68* (2017.08); *A61K 47/6815* (2017.08); *A61K 47/6851* (2017.08); *C07K 16/32* (2013.01); *C12N 9/96* (2013.01); *C12Y 305/01005* (2013.01)

(58) Field of Classification Search
CPC ........ C12N 9/80; C12N 9/96; A61K 47/6815; A61K 47/6871; A61K 47/68; A61K 47/6851; C07K 16/2863; C12Y 305/01005
See application file for complete search history.

(56) References Cited

U.S. PATENT DOCUMENTS

| | | | | |
|---|---|---|---|---|
| 4,360,592 | A * | 11/1982 | Weltman | C12N 11/06 435/5 |
| 5,587,458 | A | 12/1996 | King et al. | |
| 7,211,250 | B2 * | 5/2007 | Segal | A61K 38/50 424/94.6 |
| 9,296,819 | B2 * | 3/2016 | Uger | C07K 16/2872 |
| 2010/0203550 | A1 * | 8/2010 | Miller | G01N 33/5438 435/7.1 |

FOREIGN PATENT DOCUMENTS

| | | |
|---|---|---|
| CA | 2492472 A1 | 1/2004 |
| EP | 1 530 482 B1 | 10/2013 |
| EP | 2 324 846 B1 | 11/2014 |
| WO | WO-2013/185215 A1 | 12/2013 |

OTHER PUBLICATIONS

Strop et al., Chemistry and Biology 20: 161-167, Feb. 21, 2013.*
Stancovski et al., PNAS 88: 8691-8695, 1991.*
Yu et al., Investigative Ophthalmology & Visual Science 49(2): 522-527, Feb. 2008.*
Chandler et al., J Immunological method 53(182): 187-194, 1982.*
Tian et al., Frontiers in Immunology 8 (956): 1-19.*
Takishima et al., Eur J Biochem 175: 151-165, 1988.*
Tian et al., Frontiers in Immunology 8(956): 1-19 (Year: 2017).*
Anonymous, "Anti-mouse IgG (Whole Molecule) Urease Conjugate," Product No. U1004, SIGMA, retrieved from http://www.sigmaaldrich.com/content/dam/sigma-aldrich/docs/Sigma/Datasheet/8/u1004dat.pdf (retrieved on Oct. 20, 2016).
Baomin, T. et al., "Production and characterization of a camelid single domain antibody-urease enzyme conjugate for the treatment of cancer," Bioconjugate Chemistry, vol. 26, No. 6, pp. 1144-1155 (Jun. 17, 2015).
Chao, H., "DOS47—Killing cancer by altering the tumor microenvironment," 2011 Drug Delivery Technology USA, vol. 11, No. 1, pp. 68-72 (Jan. 2011).
Kumar, R. K., "Preparation of anti-human IgG-hrp conjugate and its use in ELISA and western blotting experiments," J. Anal. BioAnal. Techniques, vol. 3, No. 7, p. 85 (2012).
Extended European Search Report, EP 14782795.0, Helix Biopharma Corp., 12 pages (dated Nov. 3, 2016).
Chandler, et al., An investigation of the use of urease-antibody conjugates in enzyme immunoassays, Abstract, Journal of Immunological Methods, Sep. 17, 1982, vol. 53, No. 2, 1 page.
Chao, et al., Development of an alkalizing antibody-enzyme conjugate for NSCLC treatment that is in Phase I clinical setting, L-DOS47 Presentation at AACR 2013 Annual Meeting, American Association of Cancer Research, Apr. 5, 2013, 1 page.
International Search Report and Written Opinion for PCT/CA2014/050334 dated Jul. 8, 2014, 11 pages.
Winston, et al., Immunoassays: Conjugation of enzymes to antibodies, Current Protocols in Molecular Biology, Chapter 11, Units 11.1 to 11.1.7, 2000, John Wiley & Sons, Inc., 7 pages.
Wong, et al., Urease-induced alkalinization of extracellular pH and its antitumor activity in human breast and lung cancers, Journal of Experimental Therapeutics and Oncology, 2005, vol. 5, No. 2, 7 pages.
Ausubel et al., "Conjugation of Enzymes to Antibodies", Current Protocols in Molecular Biology, 2003 (8 pages).
Eminaga et al., "Quantification of microRNA Expression with Next-Generation Sequencing", Curr Protoc Mol Biol., Jul. 4, 2013: Unit-4.17 (20 pages).

* cited by examiner

*Primary Examiner* — Phuong Huynh
(74) *Attorney, Agent, or Firm* — Aird & McBurney LP

(57) ABSTRACT

This disclosure provides antibody-urease conjugates having therapeutic and diagnostic utility. More specifically, the disclosure relates to diagnostic and/or therapeutic conjugates that are prepared by conjugating one or more whole antibodies to urease.

18 Claims, No Drawings

Specification includes a Sequence Listing.

ANTIBODY-UREASE CONJUGATES

CROSS REFERENCE TO RELATED APPLICATIONS

This application is a U.S. National Phase application un 37 CFR § 371 of International Application Ser. No. PCT/CA2014/050334, filed Apr. 3, 2014, and which was published on Oct. 16, 2014 as WO2014/165985; and which claims priority to U.S. Provisional Application Ser. No. 61/809,842, filed Apr. 8, 2013, each of which are incorporated herein by reference in their entireties.

FIELD OF THE DISCLOSURE

This disclosure provides antibody-urease conjugates having therapeutic and diagnostic utility. More specifically, the disclosure relates to diagnostic and/or therapeutic conjugates that are prepared by conjugating one or more whole antibodies to urease.

BACKGROUND

Cancer accounts for one-fifth of the total mortality in the United States, and is the second leading cause of death. Cancer is typically characterized by the uncontrolled division of a population of cells. This uncontrolled division may involve blood cells, such as various types of lymphomas, or cells that aggregate in or are native to a particular tissue or organ, e.g., solid tumors, such as secondary or primary tumors of the breast, lung, liver, esophagus, stomach, intestines, brain, bone, or prostate.

A variety of treatment modalities have been proposed for cancer therapy. One such treatment modality relates to the use of particular enzymes to inhibit growth of cancer cells. One such enzyme known in the art is urease, an enzyme that catalyzes the hydrolysis of urea into carbon dioxide and ammonia. More specifically, urease catalyzes the hydrolysis of urea to produce ammonia and carbamate, the carbamate produced is subsequently degraded by spontaneous hydrolysis to produce another ammonia and carbonic acid. In this regard, urease activity tends to increase the pH of the local environment in which it is as it produces ammonia, as it is a basic molecule.

The concept of using antibodies to target tumor associated antigens in the treatment of cancer has been appreciated for some time (Herlyn et. al., (1980) Cancer Research 40, 717). However, as to urease, the toxic component is the alkaline environment produced by enzymatic degradation of urea. In such a case, the antibody employed need only to have a high binding affinity to the corresponding antigen. Although therapeutic antibodies can be used with the urease, ongoing clinical trials employ only a high affinity antibody fragment. This approach provides for several unique considerations including the fact that urease is an exceptionally large enzyme while the antibody fragments are significantly smaller. To address possible steric hinderence arising from the size of the urease, it is conventional to use multiple copies of the non-human antibody fragment.

As multiple copies of these fragments are used to ensure proper binding, limitations as to the inclusion of other components on the antibody. Moreover, as binding sites on the antibody fragment may be limited, binding of each antibody fragment to the urease is through a single tether. Still further, while immunogenicity of the antibody fragment appears to be minimal, a non-immunogenic approach would eliminate even the smallest likelihood of an adverse immune response or the need to co-administer an immunosuppressive agent.

SUMMARY

This disclosure is directed to an antibody-urease conjugate. The conjugate comprises one or two antibodies covalently bound to a urease enzyme to form an antibody-urease conjugate said conjugate optionally containing bound to either the urease or the antibody one or more therapeutic agents.

In one embodiment, provided is an antibody-urease conjugate comprising an antibody covalently bound to a urease enzyme to form an antibody-urease conjugate. In one aspect, the conjugate further comprises a therapeutic agent covalently bound to the antibody or the urease enzyme.

In one aspect, the antibody-urease conjugate comprises at least two antibodies covalently bound to the urease enzyme. In some aspects, at least one of the antibodies is covalently bound to the urease enzyme at two or more sites. In some aspects, at least one of the antibodies is covalently bound to the urease enzyme at three or more sites. In some aspects, each of the antibodies is covalently bound to the urease enzyme at two or more sites.

In some aspects, at least one of the antibodies is a full antibody. The full antibody, in some aspects, comprises at least two Fab fragments and an Fc fragment. In some aspects, the full antibody has a molecular weight that is at least 120 kDa, or 130 kDa, or 140 kDa or 150 kDa. In some aspects, the full antibody is covalently bound to the urease enzyme at two or more sites.

In some aspects, the antibodies are not directed to aberrant prions.

These and other aspects of the disclosure are further described below.

DETAILED DESCRIPTION OF THE DISCLOSURE

Definitions

It must be noted that as used herein and in the appended claims, the singular forms "a", "an", and "the" include plural referents unless the context clearly dictates otherwise. Thus, for example, reference to "a solvent" includes a plurality of such solvents.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition or process consisting essentially of the elements as defined herein would not exclude other materials or steps that do not materially affect the basic and novel characteristic(s) of the claimed disclosure. "Consisting of" shall mean excluding more than trace elements of other ingredients and substantial method steps. Embodiments defined by each of these transition terms are within the scope of this disclosure.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques. The term "about" when used before a numerical designation, e.g., temperature, time, amount, and concentration, including range, indicates approximations which may vary by (+) or (−) 10%, 5% or 1%.

The term "urease" refers to an enzyme having the enzymatic activity of a urea amidohydrolase (E.C. 3.5.1.5), either naturally occurring or obtained by, e.g., recombinant nucleic acid techniques and/or chemical synthesis. Urease also includes fusion proteins comprising the entire urease, subunits, or fragments thereof, and/or urease with amino acid substitutions, deletions or additions that preserve the urea amidohydrolase activity of the polypeptide.

A "conjugate" refers to two or more molecules that are covalently linked to form a larger construct. In some embodiments, the conjugate includes the urease enzyme bound to one or two antibodies which are covalently linked. In one aspect, the linkage is a direct linkage wherein a reactive functional group on the urease binds to a complementary reactive functional group on the antibody such as an amino functionality of lysine binding to a carboxyl functionality of aspartic or glutamic acid. It being understood, that such reactions may require conventional modification of the carboxyl group to render it more reactive.

In another aspect, the linkage is through a linker having two or more functionalities, such as carboxy or amino, that allow it to react with both the ureases and the antibody. Linkers are well known in the art and typically comprise from 1-20 atoms including carbon, nitrogen, hydrogen, oxygen, sulfur and the like. The reactive functionalities can be the same such as oxalic acid, succinic acid, and the like or can be orthogonal functionalities such as amino (which becomes NH after conjugation) and carboxyl (which becomes CO or COO after conjugation) groups.

In one aspect, a suitable linker is $R^1$-L-$R^2$, wherein $R^1$ and $R^2$ are the same or different functional groups, one of which is connected to the antibody and the other is connected to urease. $R^1$ and $R^2$ can be independently selected from —NH—, —CO—, —COO—, —O—, —S—, —N=N—, =N—NH—, etc. L can be a straight or branched-hydrocarbon chain, such as an alkyl chain, wherein one or more of the carbons are optionally replaced with oxygen, nitrogen, amide, sulfur, sulfoxide, sulfone, cycloalkyl, heterocycloalkyl, aryl, heteroaryl, etc. In another aspect, the linker can be an amino acid residue or a peptide. In some circumstances, the linker is cleavable by an enzyme or change in pH at or approximate to the target site. Certain linkers and procedures suitable for preparing conjugates are described in U.S. Pat. Nos. 4,414,148, 4,545,985, 4,569,789, 4,671,958, 4,659,839, 4,680,338, 4,699,784, 4,894,443, and 6,521,431.

The term "antibody" refers to a complete or substantially complete mammalian antibody including those obtained from mice, llamas, pigs, rats, bovine, ovine, and the like. A substantially complete antibody contains at least 90 percent homology to the complete antibody or is truncated to include the binding site of the antibody and at least 70% of the complete antibody. Antibody fragments such as those containing less than 70% of the antibody are not within the definition of antibodies in this disclosure. As used herein, an "antibody fragment" refers to a portion of a complete antibody that is less than 70% of the antibody. Preferably, the antibody recognizes a diseased antigen such as a cancer antigen. However, preferably the antigen is not a prion antigen.

The term "therapeutic agent" refers to any agent which provides for a therapeutic or prophylactic result against a given disease or disease causing agent such as a microbe. Preferably, the therapeutic agent is an anti-cancer agent such as doxorubicin, daunomycin, epirubicin, vinblastine, vincristine, mitoxantrone, bleomycin, mitomycin, mechlorethamine and the like.

The terms "treat", "treating" or "treatment", as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting or suppressing the development of the disease or condition, relieving the disease or condition, causing regression of the disease or condition, relieving a condition caused by the disease or condition, or suppressing the symptoms of the disease or condition, and are intended to include prophylaxis. The terms also include relieving the disease or conditions, e.g., causing the regression of clinical symptoms. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

Antibody-Urease Conjugates

The disclosure is directed to the conjugation of one to two or more antibodies with urease. Such conjugation is contemplated to increase the binding affinity of the antibody-urease conjugate to the antigenic target as the antibody is approximately the same size as that of urease thereby reducing significantly any steric hinderance arising from the use of antibody fragments. This increase in affinity permits the use of 1 or 2 antibodies per urease. Furthermore, the antibody-urease conjugates of the disclosure can be bound directly to the one or two antibodies, optionally through a linker. The increased size of the antibody as compared to antibody fragments permit the use of multiple sites of conjugation to stabilize the binding. In one embodiment, the conjugate includes from 1 to 8 conjugations sites between a single antibody and a single urease enzyme. In another embodiment the number of conjugation sites is from 2 to 8. In one embodiment, the conjugate includes from 2, or 3, or 4 to 8 conjugation sites between a single antibody and a single urease enzyme. In another embodiment the number of conjugation sites is at least 2, 3, or 4.

Even further, additional components, such as but not limited to, therapeutic agents such as anti-cancer agents can also be bound to the antibodies to further enhance the therapeutic effect. In one preferred embodiment, the antibody is not directed to aberrant prions.

Typically, the antibody is comparable in size to the urease which is atypical due to the large size of the urease. Heretofore, whole antibodies, which are generally about 150 kDa, necessitates the use of antibody fragments for conjugation to an enzyme so as to provide for suitable results. In this context, the inventors have discovered that due to the comparable size of the urease to the antibody, the conjugate used is advantageously an antibody-urease conjugate which allows for higher binding affinities as well as enhanced stability especially when multiple conjugation sites are employed. This is possible due to the uniquely large and amorphous size of the urease enzyme, e.g., 545 kDa for Jack Bean urease (calculated mass from the amino acid sequence). Additionally, the size of an exemplary urease also allows for multiple points of conjugation between the antibodies and the enzyme which can further stabilize the binding between the antibodies and urease, providing a 1:1, 2:1 or possibly 3:1 binding ratio of antibody:urease.

In another embodiment, the antibody-urease conjugates can be humanized as necessary to further reduce or inhibit immunological rejection.

Urease

A number of studies have provided detailed information about the genetics of ureases from a variety of evolutionarily diverse bacteria, plants, fungi and viruses (Mobley, H. L. T. et al. (1995) Microbiol. Rev. 59: 451-480; Eur J. Biochem., 175, 151-165 (1988); Labigne, A. (1990) International publication No. WO 90/04030; Clayton, C. L. et al. (1990) Nucleic Acid Res. 18, 362; and U.S. Pat. Nos. 6,248,330 and 5,298,399, each of which is incorporated herein by reference). Of particular interest is urease that is found in plants (Sirko, A. and Brodzik, R. (2000) Acta Biochim Pol 47(4): 1189-95). As mentioned above, one exemplary plant urease is jack bean urease. An exemplary amino acid sequence of jack bean urease is represented by SEQ ID NO: 1 below. Other useful urease sequences may be identified in public databases, e.g., Entrez (ncbi.nlm.nih.gov/Entrez).

In embodiments of the disclosure, the urease is jack bean urease having SEQ ID No.1, as shown below:

```
                                           (SEQ ID No. 1)
MKLSPREVEKLGLHNAGYLAQKRLARGVRLNYTEAVALIASQIM

EYARDGEKTVAQLMCLGQHLLGRRQVLPAVPHLLNAVQVEATFP

DGTKLVTVHDPISRENGELQEALFGSLLPVPSLDKFAETKEDNR

IPGEILCEDECLTLNIGRKAVILKVTSKGDRPIQVGSHYHFIEV

NPYLTFDRRKAYGMRLNIAAGTAVRFEPGDCKSVTLVSIEGNKV

IRGGNAIADGPVNETNLEAAMHAVRSKGFGHEEEKDASEGFTKE

DPNCPFNTFIHRKEYANKYGPTTGDKIRLGDTNLLAEIEKDYAL

YGDECVFGGGKVIRDGMGQSCGHPPAISLDTVITNAVIIDYTGI

IKADIGIKDGLIASIGKAGNPDIMNGVFSNMIIGANTEVIAGEG

LIVTAGAIDCHVHYICPQLVYEAISSGITTLVGGGTGPAAGTRA

TTCTPSPTQMRLMLQSTDDLPLNFGFTGKGSSSKPDELHEIIKA

GAMGLKLHEDWGSTPAAIDNCLTIAEHHDIQINIHTDTLNEAGF

VEHSIAAFKGRTIHTYHSEGAGGGHAPDIIKVCGIKNVLPSSTN

PTRPLTSNTIDEHLDMLMVCHHLDREIPEDLAFAHSRIRKKTIA

AEDVLNDIGAISIISSDSQAMGRVGEVISRTWQTADKMKAQTGP

LKCDSSDNDNFRIRRYIAKYTINPAIANGFSQYVGSVEVGKLAD

LVMWKPSFFGTKPEMVIKGGMVAWADIGDPNASIPTPEPVKMRP

MYGTLGKAGGALSIAFVSKAALDQRVNVLYGLNKRVEAVSNVRK

LTKLDMKLNDALPEITVDPESYTVKADGKLLCVSEATTVPLSRN

YFLF
```

Antibodies

As used herein, an "antibody" or "antigen-binding polypeptide" refers to a polypeptide or a polypeptide complex that specifically recognizes and binds to an antigen. An antibody can be a full antibody and any antigen binding fragment or a single chain thereof.

A "full antibody" refers to an antibody that includes, among others, two antigen-binding regions (Fab) and an Fc fragment. In some embodiments, a full antibody includes two light chains and two heavy chains.

A variety of antibodies may be employed in the practice of the disclosure. For example, both polyclonal and monoclonal antibodies may be employed. Monoclonal antibodies may be produced in accordance with conventional techniques, such as hybridoma synthesis, recombinant DNA techniques and protein synthesis.

In a preferred embodiment, the antibody is not directed to aberrant prions.

Conjugation

The antibody-urease conjugates of the disclosure can be prepared by any conventional means known in the art. For example, antibodies can be conjugated to a urease enzyme either directly or through a linker. Means of chemically conjugating molecules are well known to those of skill in the art. Methods of conjugating an antibody to urease are disclosed, for example, in U.S. Pat. Nos. 7,211,250 and 7,264,800, the contents of which are incorporated herein by reference in their entirety.

Stabilizing Ureases

Methods are also provided, in some embodiments, to stabilize urease enzymes by conjugating a urease enzyme with one or two or more antibodies for a urease enzyme-antibody conjugate as described in the present disclosure. Such conjugation is contemplated to increase the binding affinity of the antibody-urease conjugate to the antigenic target as the antibody is approximately the same size as that of urease thereby reducing significantly any steric hinderance arising from the use of antibody fragments. This increase in affinity permits the use of 1 or 2 antibodies per urease. Furthermore, the antibody-urease conjugates of the disclosure can be bound directly to the one or two antibodies, optionally through a linker. The increased size of the antibody as compared to antibody fragments permit the use of multiple sites of conjugation to stabilize the binding. In one embodiment, the conjugate includes from 1 to 8 conjugations sites between a single antibody and a single urease enzyme. In another embodiment the number of conjugation sites is from 2 to 8. In one embodiment, the conjugate includes from 2, or 3, or 4 to 8 conjugation sites between a single antibody and a single urease enzyme. In another embodiment the number of conjugation sites is at least 2, 3, or 4.

In some embodiments, the antibody and urease enzyme form at least a bond, such as a covalent or an ionic bond that prevents or decreases dissociation between the antibody and the urease. In one aspect, the bond is labile, such that the bond will degrade at certain in vivo environment (e.g., near a tumor cell wherein the pH is different from normal tissue). In another aspect, the bond is non-labile and stable at normal physiological conditions.

EXAMPLES

The following examples are given for the purpose of illustrating various embodiments of the disclosure. They are not meant to limit the disclosure in any fashion. One skilled in the art will appreciate that the disclosure is well adapted to carry out the objects and obtain the ends and advantages mentioned, as well any objects, ends and advantages inherent herein. The present examples (along with the methods described herein) are presently representative of preferred embodiments. They are exemplary, and are not intended as limitations on the scope of the disclosure. Variations and other uses which are encompassed within the spirit of the disclosure as defined by the scope of the claims will occur to those skilled in the art.

Example 1

An antibody-urease conjugate is prepared by conjugating anti-ErbB2 monoclonal antibody 4D5 with urease using SIAB (succinimidyl-(4-iodoacetyl)aminobenzoate) as a linker. SIAB is a mid-length crosslinker for amine-to-sulfhydryl conjugation via N-hydroxysuccinimide (NHS) ester and iodoacetyl reactive groups. It yields a spacer arm of about 10.6 Angstroms in length. It is available commercially from Thermo Scientific, and its use in conjugation is described for instance by Hermanson, Bioconjugate Techniques, 1996, San Diego, Academic Press pp. 542, 553, 568. The degree of conjugation can be increased by increasing the amount of linker used relative to the antibody. Furthermore, the antibody can be first treated with the linker by using multiple equivalents of linker, the combination of which can thereafter be combined with urease.

First, anti-ErbB2 monoclonal antibody 4D5 was activated with SIAB (molar ratio SIAB:IgG=3.8:1) at the pH of the original buffer matrix, for 70 minutes. The reaction was then quenched for ten minutes at room temperature with addition of Tris-HCl buffer, to a final concentration of 5 mM. The resulting solution was chilled with ice/water, and chilled high purity urease (5 mg/ml, ~0C, GMP grade jack bean urease) was added while vortexing. Protein molar ratios were 1:2/IgG:HPU. Tris-HCl (200 mM, pH 8.45) was added at 1/10 volume to adjust the pH to 8.0-8.3, over a period of 90 minutes. For stability, hydrolyzed SIAB was added to coup most of the surface hydrosulfite of urease. The molar ratio was 1:7 (urease:hydro-SIAB), room temperature, 30 minutes. The reaction was then quenched by adding cysteine solution (100 mM in 200 mM Tris-HCl buffer, pH 8.45) to a final concentration of 5 mM, room temperature, 10 minutes. The resulting mixture was subjected to SEC separation with a GE healthcare Superose 6 10/300 column, and the fractions were collected. Fractions F10-13 minutes were pooled and dialyzed (MWCO 12-14 kD) against 20 mM arginine buffer containing 1% sucrose and 0.2 mM EDTA, pH 7.0. Collected samples were then analyzed by SDS-PAGE, by protein assay with BCA protocol, by urease-enzyme activity assay with the tube protocol, and by ELISA binding assay to reveal the conjugate is active.

From the foregoing it will be appreciated that, although specific embodiments of the disclosure have been described herein for purposes of illustration, various modifications may be made without deviating from the spirit and scope of the disclosure.

Throughout the description of this disclosure, reference is made to various patent applications and publications, each of which are herein incorporated by reference in their entirety.

What is claimed is:

1. An antibody-urease conjugate comprising at least one antibody covalently bound to a jack bean urease enzyme, wherein the antibody has a molecular weight that is at least 150 kDa, wherein the antibody is not directed to an aberrant prion, the antibody having two or more sites of conjugation through one or more linker(s) to the jack bean urease enzyme to stabilize binding of the antibody to said jack bean urease enzyme, and further wherein said antibody-urease conjugate is formed by;
 first treating the antibody with multiple equivalents of linker succinimidyl-(4-iodoacetyl)aminobenzoate (SIAB) in a molar ratio of about 3.8:1 (linker:antibody);
 adding the jack bean urease to form the antibody-urease conjugate; and
 adding an excess molar ratio of hydrolyzed linker to stabilize said formed antibody-urease conjugate.

2. The antibody-urease conjugate of claim 1, further comprising a therapeutic agent covalently bound to the antibody or the jack bean urease enzyme.

3. The antibody-urease conjugate of claim 1, comprising at least two antibodies covalently bound to the urease enzyme.

4. The antibody-urease conjugate of claim 3, wherein at least one of the two antibodies is a full antibody.

5. The antibody-urease conjugate of claim 4, wherein the full antibody comprises at least two Fab fragments and an Fc fragment.

6. The antibody-urease conjugate of claim 4, wherein the full antibody includes two light chains and two heavy chains.

7. The antibody-urease conjugate of claim 1, wherein the antibody is covalently bound to the urease enzyme at three or more sites.

8. The antibody-urease conjugate of claim 3, wherein the two antibodies are not directed to aberrant prions.

9. A method for stabilizing a jack bean urease enzyme with an antibody, said method comprising conjugating the jack bean urease enzyme with at least one antibody at two or more conjugation sites to form a stabilized antibody-urease conjugate, wherein said at least one antibody has a molecular weight that is at least 150 kDa and said at least one antibody is not directed to an aberrant prion,
 wherein said stabilized antibody-urease conjugate is formed by:

first treating the at least one antibody with multiple equivalents of a linker succinimdyl-(4-iodoacetyl) aminobenzoate (SIAB) in a molar ratio of about 3.8:1 (linker:antibody);

adding the jack bean urease to form the antibody-urease conjugate; and adding an excess molar ratio of hydrolyzed linker to stabilize said jack bean urease and form the stabilized antibody-urease conjugate.

10. The method of claim 9, wherein the jack bean urease enzyme is conjugated to the at least one antibody at two to eight conjugation sites.

11. The method of claim 9, wherein the jack bean urease enzyme has a molecular weight of about 545 kDa.

12. The method of claim 9, wherein the hydrolyzed linker is provided in a molar ratio of about 1:7 (urease:SIAB).

13. The method of claim 9, comprising conjugating the jack bean urease enzyme with two or more antibodies each one of said antibodiesy at two or more conjugation sites to form a stabilized jack bean urease enzyme antibody-urease conjugate.

14. The antibody-urease conjugate of claim 1, wherein the hydrolyzed linker is provided in a molar ratio of about 1:7 (urease:SIAB).

15. The antibody-urease conjugate of claim 3, wherein each of said two antibodies is covalently bound to the urease enzyme at two or more conjugation sites.

16. The antibody-urease conjugate of claim 15, wherein at least one of the at least two antibodies is covalently bound to the urease enzyme at three or more conjugation sites.

17. The antibody-urease conjugate of claim 1, wherein said jack bean urease enzyme has a molecular weight of about 545 kDa.

18. The antibody-urease conjugate of claim 17, wherein said jack bean urease enzyme has SEQ ID No:1.

\* \* \* \* \*

```
                        SEQUENCE LISTING

<160> NUMBER OF SEQ ID NOS: 1

<210> SEQ ID NO 1
<211> LENGTH: 840
<212> TYPE: PRT
<213> ORGANISM: Unknown
<220> FEATURE:
<223> OTHER INFORMATION: Jack bean urease

<400> SEQUENCE: 1

Met Lys Leu Ser Pro Arg Glu Val Glu Lys Leu Gly Leu His Asn Ala
1               5                   10                  15

Gly Tyr Leu Ala Gln Lys Arg Leu Ala Arg Gly Val Arg Leu Asn Tyr
            20                  25                  30

Thr Glu Ala Val Ala Leu Ile Ala Ser Gln Ile Met Glu Tyr Ala Arg
        35                  40                  45

Asp Gly Glu Lys Thr Val Ala Gln Leu Met Cys Leu Gly Gln His Leu
    50                  55                  60

Leu Gly Arg Arg Gln Val Leu Pro Ala Val Pro His Leu Leu Asn Ala
65                  70                  75                  80

Val Gln Val Glu Ala Thr Phe Pro Asp Gly Thr Lys Leu Val Thr Val
                85                  90                  95

His Asp Pro Ile Ser Arg Glu Asn Gly Glu Leu Gln Glu Ala Leu Phe
            100                 105                 110

Gly Ser Leu Leu Pro Val Pro Ser Leu Asp Lys Phe Ala Glu Thr Lys
        115                 120                 125

Glu Asp Asn Arg Ile Pro Gly Glu Ile Leu Cys Glu Asp Glu Cys Leu
    130                 135                 140

Thr Leu Asn Ile Gly Arg Lys Ala Val Ile Leu Lys Val Thr Ser Lys
145                 150                 155                 160
```

```
Gly Asp Arg Pro Ile Gln Val Gly Ser His Tyr His Phe Ile Glu Val
            165                 170                 175
Asn Pro Tyr Leu Thr Phe Asp Arg Arg Lys Ala Tyr Gly Met Arg Leu
        180                 185                 190
Asn Ile Ala Ala Gly Thr Ala Val Arg Phe Glu Pro Gly Asp Cys Lys
            195                 200                 205
Ser Val Thr Leu Val Ser Ile Glu Gly Asn Lys Val Ile Arg Gly Gly
        210                 215                 220
Asn Ala Ile Ala Asp Gly Pro Val Asn Glu Thr Asn Leu Glu Ala Ala
225                 230                 235                 240
Met His Ala Val Arg Ser Lys Gly Phe Gly His Glu Glu Lys Asp
            245                 250                 255
Ala Ser Glu Gly Phe Thr Lys Glu Asp Pro Asn Cys Pro Phe Asn Thr
            260                 265                 270
Phe Ile His Arg Lys Glu Tyr Ala Asn Lys Tyr Gly Pro Thr Thr Gly
            275                 280                 285
Asp Lys Ile Arg Leu Gly Asp Thr Asn Leu Leu Ala Glu Ile Glu Lys
            290                 295                 300
Asp Tyr Ala Leu Tyr Gly Asp Glu Cys Val Phe Gly Gly Lys Val
305                 310                 315                 320
Ile Arg Asp Gly Met Gly Gln Ser Cys Gly His Pro Pro Ala Ile Ser
                325                 330                 335
Leu Asp Thr Val Ile Thr Asn Ala Val Ile Asp Tyr Thr Gly Ile
            340                 345                 350
Ile Lys Ala Asp Ile Gly Ile Lys Asp Gly Leu Ile Ala Ser Ile Gly
            355                 360                 365
Lys Ala Gly Asn Pro Asp Ile Met Asn Gly Val Phe Ser Asn Met Ile
        370                 375                 380
Ile Gly Ala Asn Thr Glu Val Ile Ala Gly Glu Gly Leu Ile Val Thr
385                 390                 395                 400
Ala Gly Ala Ile Asp Cys His Val His Tyr Ile Cys Pro Gln Leu Val
                405                 410                 415
Tyr Glu Ala Ile Ser Ser Gly Ile Thr Thr Leu Val Gly Gly Gly Thr
            420                 425                 430
Gly Pro Ala Ala Gly Thr Arg Ala Thr Thr Cys Thr Pro Ser Pro Thr
            435                 440                 445
Gln Met Arg Leu Met Leu Gln Ser Thr Asp Asp Leu Pro Leu Asn Phe
            450                 455                 460
Gly Phe Thr Gly Lys Gly Ser Ser Ser Lys Pro Asp Glu Leu His Glu
465                 470                 475                 480
Ile Ile Lys Ala Gly Ala Met Gly Leu Lys Leu His Glu Asp Trp Gly
                485                 490                 495
Ser Thr Pro Ala Ala Ile Asp Asn Cys Leu Thr Ile Ala Glu His His
            500                 505                 510
Asp Ile Gln Ile Asn Ile His Thr Asp Thr Leu Asn Glu Ala Gly Phe
            515                 520                 525
Val Glu His Ser Ile Ala Ala Phe Lys Gly Arg Thr Ile His Thr Tyr
            530                 535                 540
His Ser Glu Gly Ala Gly Gly Gly His Ala Pro Asp Ile Ile Lys Val
545                 550                 555                 560
Cys Gly Ile Lys Asn Val Leu Pro Ser Ser Thr Asn Pro Thr Arg Pro
                565                 570                 575
Leu Thr Ser Asn Thr Ile Asp Glu His Leu Asp Met Leu Met Val Cys
```

-continued

|     |     |     |     |     | 580 |     |     |     | 585 |     |     |     |     | 590 |     |     |     |
| --- | --- | --- | --- | --- | --- | --- | --- | --- | --- | --- | --- | --- | --- | --- | --- | --- | --- |

His His Leu Asp Arg Glu Ile Pro Glu Asp Leu Ala Phe Ala His Ser
         595                 600                 605

Arg Ile Arg Lys Lys Thr Ile Ala Ala Glu Asp Val Leu Asn Asp Ile
         610             615                 620

Gly Ala Ile Ser Ile Ile Ser Ser Asp Ser Gln Ala Met Gly Arg Val
625              630                 635                 640

Gly Glu Val Ile Ser Arg Thr Trp Gln Thr Ala Asp Lys Met Lys Ala
                 645                 650                 655

Gln Thr Gly Pro Leu Lys Cys Asp Ser Ser Asp Asn Asp Asn Phe Arg
             660             665                 670

Ile Arg Arg Tyr Ile Ala Lys Tyr Thr Ile Asn Pro Ala Ile Ala Asn
         675             680                 685

Gly Phe Ser Gln Tyr Val Gly Ser Val Glu Val Gly Lys Leu Ala Asp
        690              695                 700

Leu Val Met Trp Lys Pro Ser Phe Phe Gly Thr Lys Pro Glu Met Val
705             710                 715                 720

Ile Lys Gly Gly Met Val Ala Trp Ala Asp Ile Gly Asp Pro Asn Ala
                725                 730                 735

Ser Ile Pro Thr Pro Glu Pro Val Lys Met Arg Pro Met Tyr Gly Thr
             740             745                 750

Leu Gly Lys Ala Gly Gly Ala Leu Ser Ile Ala Phe Val Ser Lys Ala
        755                 760                 765

Ala Leu Asp Gln Arg Val Asn Val Leu Tyr Gly Leu Asn Lys Arg Val
770                 775                 780

Glu Ala Val Ser Asn Val Arg Lys Leu Thr Lys Leu Asp Met Lys Leu
785             790                 795                 800

Asn Asp Ala Leu Pro Glu Ile Thr Val Asp Pro Glu Ser Tyr Thr Val
                805             810                 815

Lys Ala Asp Gly Lys Leu Leu Cys Val Ser Glu Ala Thr Thr Val Pro
            820                 825             830

Leu Ser Arg Asn Tyr Phe Leu Phe
        835             840